United States Patent [19]

Tsukamoto et al.

[11] 3,954,227

[45] May 4, 1976

[54] PHARMACEUTICAL COMPOSITIONS CONTAINING 1-(2',3'-DIMETHYLPHENOXY)-3-TERT. BUTYLAMINO-2-PROPANOL OR PHARMACEUTICALLY ACCEPTABLE SALT THEREOF FOR TREATING OR PREVENTING CORONARY DISORDERS

[75] Inventors: Kunio Tsukamoto, Tokyo; Yasushi Suzuki, Yokohama; Akihiro Izumi, Kawasaki; Yoshio Hiramatsu, Tokyo, all of Japan

[73] Assignee: Teikoku Hormone Mfg. Co., Ltd., Tokyo, Japan

[22] Filed: Jan. 16, 1973

[21] Appl. No.: 324,100

Related U.S. Application Data

[63] Continuation-in-part of Ser. No. 92,252, Nov. 23, 1970.

[30] Foreign Application Priority Data

Nov. 28, 1969 Japan.............................. 44-95027
Mar. 31, 1970 Japan.............................. 45-26548
Mar. 31, 1970 Japan.............................. 45-26549
July 21, 1970 Japan.............................. 45-63377
Oct. 16, 1970 Japan.............................. 45-90429
Nov. 13, 1970 Japan.............................. 45-99733

[52] U.S. Cl.............................. 424/330; 424/280
[51] Int. Cl.$^2$.................................... A61K 31/125
[58] Field of Search........................... 424/330, 280

[56] References Cited
FOREIGN PATENTS OR APPLICATIONS
1,236,523  3/1967  Germany.................... 260/570.7

*Primary Examiner*—Albert T. Meyers
*Assistant Examiner*—Daren M. Stephens
*Attorney, Agent, or Firm*—Sherman & Shalloway

[57] ABSTRACT

A method of treating or preventing coronary disorders by the administration orally or rectally of a pharmaceutical preparation containing 1-(2',3'-dimethylphenoxy)-3-tert. butylamino-2-propanol or a salt thereof.

10 Claims, No Drawings

PHARMACEUTICAL COMPOSITIONS CONTAINING 1-(2',3'-DIMETHYLPHENOXY)-3-TERT.-BUTYLAMINO-2-PROPANOL OR PHARMACEUTICALLY ACCEPTABLE SALT THEREOF FOR TREATING OR PREVENTING CORONARY DISORDERS

This application is a continuation-in-part of application Ser. No. 92,252 filed Nov. 23, 1970.

This invention relates to a method of treating or preventing coronary disorders and, in particular, to a method of treating or preventing coronary disorders by administering via the intestinal absorption route a pharmaceutical composition containing 1-(2',3'-dimethylphenoxy)-3-tert. butylamino-2-propanol.

Various 1-aryloxy-3-alkylamino-2-propanol derivatives have been known as having the beta-adrenergic blocking activity and hence as being useful as pharmaceutical preparations for treating or preventing the coronary disorders (see, for example, Belgian Pat. No. 641,133).

However, these known 1-aryloxy-3-alkylamino-2-propanol derivatives, when administered to the human body, have the shortcoming that they cause a drop in the heart rate and hence have a tendency of causing heart failure.

It has now been found that by administering via the intestinal absorption route a pharmaceutical preparation having as its active ingredient the compound 1-(2',3'-dimethylphenoxy)-3-tert. butylamino-2-propanol (for brevity to be hereinafter referred to, at times, as compound A) of the following formula, a beta-adrenergic blocking activity is demonstrated without hardly any effect on the heart rate, with the consequence that the treatment or prevention of coronary disorders can be carried out with safety.

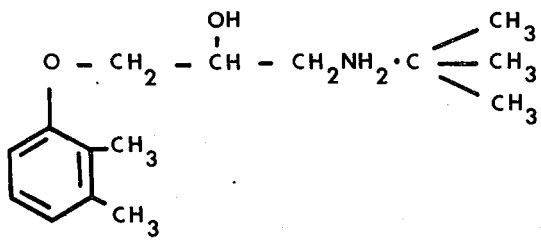

The present invention is therefore directed to a method of blocking the activity of the beta-adrenergic nerve by administering to the human body via the intestinal absorption route a compound of the formula

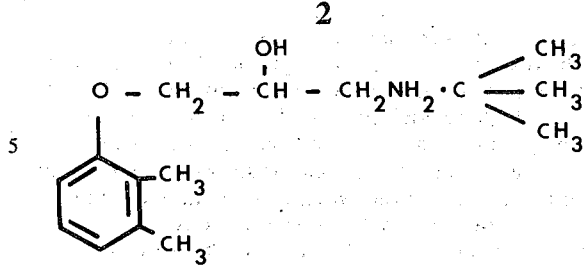

or a salt thereof in a dosage in the range of 0.5 – 100 mg thereby effecting the cure or prevention of coronary disorders.

The terminology "administration via the intestinal absorption route", as used herein, is meant to be oral and rectal administrations.

When the other 1-aryloxy-3-alkylamino-2-propanols having a chemical structure similar to that of the compound A, the active ingredient of the pharmaceutical composition of the present invention, are used in treating coronary disorders, whether the administration is by injection or by intestinal absorption, there occurs a marked drop in the heart rate to bring about heart failure and, at times, death. Again, when the active ingredient compound A of the invention pharmaceutical composition is administered by injection, a drop in heart rate likewise takes place.

Hence, it is truly surprising that the beta-adrenergic blocking activity is demonstrated without bringing about a drop in heart rate only when the invention pharmaceutical composition having the compound A as its active ingredient is administered orally.

Moreover, when the pharmaceutical composition containing the invention active ingredient compound A is administered orally, it demonstrates, as compared with the 1-aryloxy-3-alkylamino-2-propanols, which have a chemical structure similar to that of the compound A, a beta-adrenergic blocking activity that is exceedingly high. For instance, in an experiment using dogs, the beta-adrenergic blocking activity demonstrated by the invention composition is about 11 times that of PROPRANOLOL, which is known as being 1-naphthoxy-3-isopropylamino-2-propanol. On the other hand, since the beta-adrenergic blocking activity of the invention pharmaceutical composition containing the compound A is only about two times that of PROPRANOLOL when administered intravenously, it was truly unexpected that the invention would demonstrate such a marked activity when administered orally.

It is demanded of a preparation possessing the beta-adrenergic blocking activity that it be one which checks an increase of heart rate resulting from the physical activity of the patient but does not affect the normal heart rate. The foregoing demand is satisfied by the invention pharmaceutical composition containing the active ingredient compound A, since the normal heart rate is hardly affected at all when it is administered orally while, on the other hand, a high beta-adrenergic blocking activity is demonstrated. Hence, the invention pharmaceutical preparation, which is a pharmaceutical composition that is administered via the intestinal absorption route, is one whose safety is very high, i.e., it is a pharmaceutical composition possessing a beta-adrenergic blocking activity that can be safely administered over wide ranges of dosages.

The reason why the active ingredient compound A of the invention pharmaceutical composition demonstrated a high beta-adrenergic blocking activity without bringing about a drop in the heart rate only when it is administered via the intestinal absorption route is not exactly clear. However, when compound A is administered via the intestinal absorption route, e.g. orally, there are produced as metabolic products of the compound A a compound B of the formula

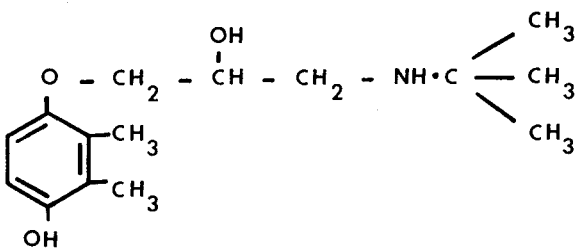

and a compound C of the formula

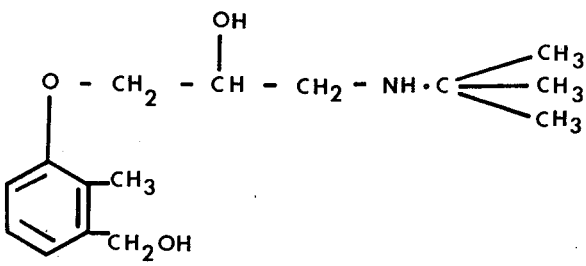

and since these metabolic products also possess the beta-adrenergic blocking activity, it is presumed in all probability that this is due to the synergistic action of the compound A and these metabolic products.

The compound A has been known prior to the present invention, and it is also known that this substance possesses beta-adrenergic blocking activity. (See, for example, German Patent Publication DAS 1,236,523).

However, the administration of a pharmaceutical preparation containing this substance via the intestinal absorption route is not known. Further, the advantages that are obtained when a pharmaceutical preparation containing this substance is administered, say, orally, as compared with the case where the other known 1-aryloxy-3-alkylamino-2-propanol derivatives are orally administered and the case where the compound A is administered by means of injection, are also not known.

In administering the invention pharmaceutical composition containing the compound A, pharmaceutical preparations of conventional forms can be used. As those usually used, those in the form of either a powder, granules, tablets, microcapsules, capsules, syrup and suppository can be used.

When used in the powder form, the compound A can be diluted with a diluent that is usually used when administering in powder form such, for example, as lactose, sucrose, dextrose, levulose, starch, microcrystalline cellulose and the like and then administered in easily administrable doses.

On the other hand, when the invention pharmaceutical composition is to be used in solution form, the compound A can be dissolved in a liquid diluent suitably used as an aqueous agent, e.g., purified water, an aqueous sucrose solution or an aqueous solution containing a sweetening agent (a solution containing in a suitable concentration as the sweetening agent the saccharides other than the foregoing surcrose, e.g., dextrose and levulose and the artificial sweetening agent such as saccharin and the sweetening agent obtained from the peptides) or be dissolved in the foregoing aqueous solutions containing sorbitol, glycerin or ethanol. Further, the compound A can be used in suspension in the form of microcapsules.

Now, if in this case honey, millet honey, white sugar syrup and the like are used, an easily administrable aqueous preparation can be prepared which suits the patient's liking. On the other hand, in the case where the compound A is to be used in the form of a suspension, the suspension of the compound in a liquid medium that can be used for oral administration will do, but in the case of a microcapsule suspension, a compound A-containing microcapsule obtained by the coacervation method can be used. In this case, as examples of the suspension medium, preferred are gum arabic, methyl cellulose, sodium carboxymethylcellulose and sodium alginate, which may be added in suitable amounts. Further, in the case also of a suppository, the preparation thereof can be accomplished by the customary procedure, incorporating the invention compound A. Thus, all of the forms of pharmaceutical preparations described above can be prepared by the known production methods.

The invention pharmaceutical composition to be used for administration via the intestinal absorption route contains as its requisite ingredient either the active ingredient compound A or its addition salt.

The active ingredient compound A of the instant invention can be prepared by the known method disclosed in German Patent Publication 1,236,523; i.e., by such methods as:

a. Reacting tert. butylamine with a compound of the formula

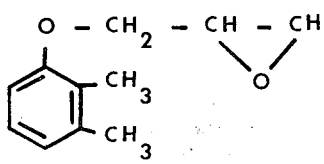

or a compound of the formula

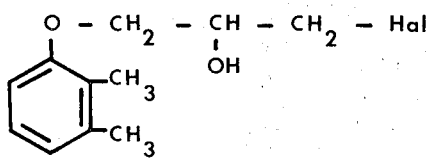

b. Reacting either 1-tert. butylamino-2,3-epoxipropane or 1-tert. butylamino-2-hydroxy-propane-halogenide-(3) with 2,3-dimethylphenol.

c. Reacting a tert. butyl halogenide with a compound of the formula

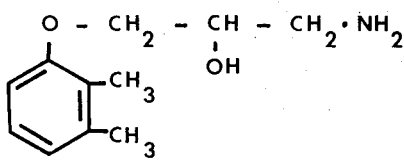

d. Reducing a compound of the formula

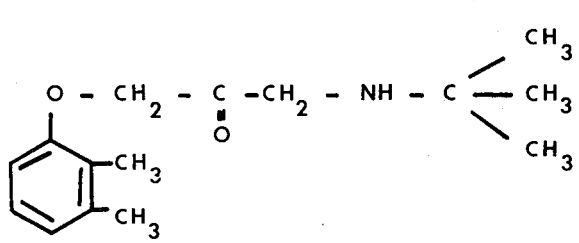

However, the active ingredient compound A can be advantageously prepared by the method developed by the present applicants and disclosed in our copending application U.S. Ser. No. 92,252; i.e., by reacting 2,3-dimethylphenol with 1-tert. butyl-3-azetidinol.

The invention active ingredient compound A can be converted into its acid addition salts by any convenient method. Suitable acids are, for example, hydrochloric acid, hydrobromic acid, sulphuric acid, phosphoric acid, methanesulphonic acid, acetic acid, lactic acid, tartaric acid and ascorbic acid.

Pharmacological tests have been carried out designed to compare the pharmacological properties of compound A with those of the related known compounds.

EXPERIMENTAL METHOD.

1. Beta-adrenergic blocking activity in the case of intravenous injection (Antagonism to heart rate increase due to ISOPROTERENOL)

a. Male rats of Wistar strain weighing ca. 300 grams were anesthetized with PENTOBARBITAL-Na (60 mg/kg i.p.), after which they are secured in a supine position. The electrocardiogram was registered in the second lead, on a polygraph. ISOPROTERENOL (0.1 µg/kg) was administered through the left femoral vein at 7-minute intervals.

The heart rate increase for the first two times was averaged and used as control.

The antagonistic chemical was intravenously injected from the third time the ISOPROTERENOL was administered, the administration being performed cumulatively and sequentially in the amounts of respectively 6.25, 25, 100 ... µg/kg invariably at a point 2 minutes before each administration of ISOPROTERENOL until the effects thereof practically disappeared.

The relative potency of the several chemicals to PROPRANOLOL was calculated relatively from the 50% antagonistic dose ($ED_{50}$) of the several chemicals with respect to the ISOPROTERENOL reaction.

b) Mongrel dogs weighing ca. 12 kg were anesthetized with PENTOBARBITAL-Na (30 mg/kg i.v.). The vagus nerves on both sides were then severed, and the femoral arterial pressure and the electrogram (lead II) were recorded on a polygraph. ISOPROTERENOL (0.3 µg/kg) was administered through the left femoral vein at 15-minutes intervals. The heart rate increase that occurs at the first administration was used as control. The antagonistic chemical was injected intravenously from the second time the ISOPROTERENOL was administered, the administration being performed cumulatively and sequentially in the amounts of respectively 1.0, 3.0, 10, 30, ... µg/kg invariably at a point 5 minutes before each administration of ISOPROTERENOL until the effects thereof practically disappeared.

The relative potency to PROPRANOLOL was calculated relatively from the 50% antagonistic dose of the several chemicals with respect to the ISOPROTERENOL reaction.

2. The beta-adrenergic blocking activity in the case of oral administration.

a. Male rats of the Donryu strain weighing ca. 250 grams, after fasting for 17 - 23 hours, were administered orally with a beta-adrenergic blocking agent (saline was administered to the control rats). The rats were then anesthetized 45 minutes later with PENTOBARBITAL-Na (60 mg/kg i.p.), and the electrograms (lead II) were recorded on a polygraph. Next, the chemicals were administered, and one hour later ISOPROTERENOL (0.1 µg/kg) was intravenously injected three times at 10-minute intervals, the increase in heart rate being recorded.

The relative potency to PROPRANOLOL was determined by comparing the reaction of ISOPROTERENOL in the saline-administered rats (control) with the reaction in the chemical-administered rats and calculating from the chemical dosage required for the latter to effect a 50 % suppression of the former.

b. Mongrel male dogs weighing ca. 1.0 kg, after fasting for 24 hours, were orally administered with chemicals placed in gelatin capsules along with 50 mg/head of lactose (the control group being administered only lactose). The dogs were then anesthetized with PENTOBARBITAL-Na (30 mg/kg i.v.) and, after severing the vagus nerves on both sides, the femoral arterial pressure and electrogram (lead II) were recorded on a polygraph. During the period 2 to 5 hours after the antagonistic chemical was administered, ISOPROTERENOL (0.3 μg/kg i.v.) was administered at 15-minute intervals during the first hour and at 30-minute intervals during the next 2 hours, and the increase in heart rate and drop in blood pressure were recorded.

The relative potency to PROPRANOLOL was calculated from the $ED_{50}$ value obtained by comparing the value obtained in the case of the ISOPROTERENOL reaction of the control group administered the lactose with that of the group administered the chemicals.

3. Behavior analysis.
  a. Mouse.
    The effects of chemicals on the behavior of mouse was examined by a simplified method of Irwin's multidimensional behavior analysis method.

Male mice of the dd strain (weight 18 – 22 grams) were placed in observation jars, three mice to a group, and their behaviors were observed for 4 hours after oral administration of the chemical.

b. Rat.
  Male rats of the Donryu strain weighing 200 – 260 grams were placed in observation jars, one to each jar, and they were observed for general symptoms by a method similar to that used in the case of mice. The chemical to be tested was administered orally, and observations of the behaviors of the rats were carried out for 4 hours after administration of the chemical.

One group consisted of three rats.

The results obtained in the foregoing experiments: (1) the beta-adrenergic blocking activity in the case of intravenous injection, (2) the beta-adrenergic blocking activity in the case of oral administration and (3) the behavior analysis, as well as the lethal dosages of the chemicals when administered orally to rats and dogs and the rate of heart rate drop when administered in the amount required for manifesting the beta-adrenergic blocking activity [$ED_{50}$] are shown in Table 1.

Table 1

| | Beta-adrenergic blocking activity | | | | | |
|---|---|---|---|---|---|---|
| | Rat | | | Dog | | |
| | Relative effectiveness | | $ED_{50}$ (PO) | Relative effectiveness | | $ED_{50}$ (PO) |
| Chemical | iv | PO | | iv | PO | |
| 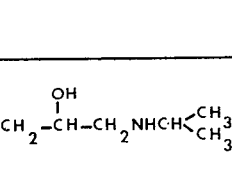 PROPRANOLOL | 1.0 | 1.0 | 14mg | 1.0 | 1.0 | 2mg |
| 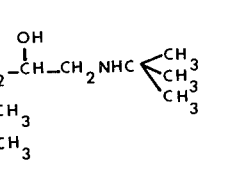 Invention compound A | 2.0 | 7.0 | 2mg | 1.5 | 11.0 | 0.18mg |
| 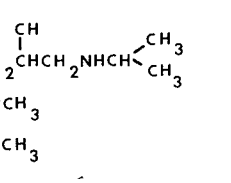 | 1.2 | 2.0 | 7mg | 1.0 | 1.8 | 1.1mg |
| 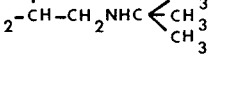 | 0.4 | 0.6 | 23mg | 0.5 | 0.7 | 2.9mg |

Table 1-continued

| Chemical | Beta-adrenergic blocking activity | | | | | |
|---|---|---|---|---|---|---|
| | Rat | | | Dog | | |
| | Relative effectiveness | | $ED_{50}$ (PO) | Relative effectiveness | | $ED_{50}$ (PO) |
| | iv | PO | | iv | PO | |
| 3,5-dimethylphenoxy, OH, NHC(CH₃)₃ | 0.6 | 0.8 | 18mg | — | — | — |
| 3-methylphenoxy, OH, NHCH(CH₃)₂ | 0.8 | 0.8 | 18mg | — | — | — |
| 3-methylphenoxy, OH, NHC(CH₃)₃ | 1.0 | 0.9 | 16mg | 1.2 | 1.0 | 2mg |
| 2-allylphenoxy, OH, NHCH(CH₃)₂ | 2.3 | 2.8 | 5mg | 2.0 | 2.0 | 1mg |
| 2,3-dichlorophenoxy, OH, NHCH(CH₃)₂ | 0.5 | 0.6 | 23mg | — | — | — |
| 2-propenylphenoxy, OH, NHC(CH₃)₃ | 2.5 | 1.5 | 9.5mg | — | — | — |
| 2-acetamidophenoxy, OH, NHC(CH₃)₃ | 0.25 | 0.5 | 28mg | — | — | — |

3,954,227

Table I-continued

| Chemical | Side reactions 1) Dose at which effects appeared from the standpoints of behavior analysis (PO) | | 2) LD$_{50}$ | | Heart rate drop at the dosage required for manifestation of beta-adrenergic blocking activity [ED$_{50}$] No/min. [value iv ( )=% drop] | | | |
|---|---|---|---|---|---|---|---|---|
| | Mouse | Rat | Rat | Dog | iv Rat | Dog | PO Rat | Dog |
| 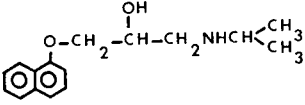 PROPRANOLOL | 100mg | 25mg | 420mg | 180mg | 60 (16%) | 25 (17%) | 80 (22%) | 30 (20%) |
| 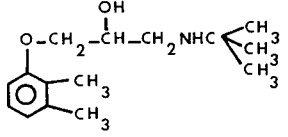 Invention compound A | 200mg | 50mg | 580mg | 300mg | 55 (15%) | 23 (16%) | 15 (4%) | 3 (2%) |
| 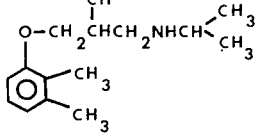 | 150mg | 30mg | 500mg | — | 60 (16%) | 23 (16%) | 70 (19%) | 15 (10%) |
| 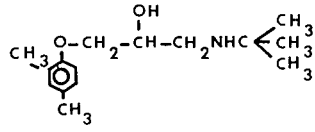 | 100mg | 30mg | 660mg | — | 65 (18%) | 26 (18%) | 90 (24%) | 20 (13%) |
| 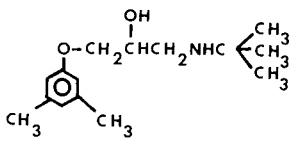 | — | — | — | — | 47 (13%) | — | 56 (15%) | — |
| 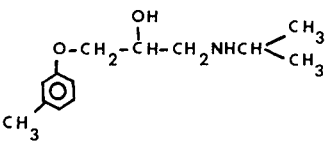 | — | — | — | — | — | — | — | — |
| 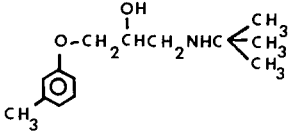 | 200mg | 60mg | 650mg | — | — | — | — | — |

Table 1-continued

| Chemical | Side reactions 1) Dose at which effects appeared from the standpoints of behavior analysis (PO) | | 2) LD$_{50}$ | | Heart rate drop at the dosage required for manifestation of beta-adrenergic blocking activity [ED$_{50}$] No/min. [value iv( )=% drop] | | | |
|---|---|---|---|---|---|---|---|---|
| | Mouse | Rat | Rat | Dog | iv Rat | Dog | PO Rat | Dog |
| structure 1: O-CH$_2$-CHCH$_2$NHCH(CH$_3$)$_2$ with OH, ring substituted with -CH$_2$CH=CH$_2$ | 140mg | 40mg | — | — | — | — | — | — |
| structure 2: O-CH$_2$CHCH$_2$NHCH(CH$_3$)$_2$ with OH, ring substituted with Cl, Cl | — | — | — | — | — | — | — | — |
| structure 3: O-CH$_2$CHCH$_2$NHC(CH$_3$)$_3$ with OH, ring substituted with -CH=CH-CH$_3$ | — | — | — | — | — | — | — | — |
| structure 4: O-CH$_2$CHCH$_2$NHC(CH$_3$)$_3$ with OH, ring substituted with NHCOCH$_3$ | — | — | — | — | — | — | — | — |

As is apparent from the Table 1, above, the oral 50 % antagonistic dose (ED$_{50}$) of the invention compound is 2 mg in rats and 0.18 mg in dogs. When this is compared with the dosages of 14 mg and 2 mg, respectively, in the case of PROPRANOLOL, the relative potency to propanolol demonstrated is about 7 in rats, and about 11 in dogs. Thus, a strong beta-adrenergic blocking activity was demonstrated, an effectiveness quite unexpected when considered from the fact that when given intravenously the relative potency was 2 in rats and 1.5 in dogs.

Further, when the oral beta-adrenergic blocking activity of the other compounds having this activity is compared with that of the invention compound A, it can be appreciated that the beta-adrenergic blocking activity of the invention compound A is outstandingly superior.

When the decrease in heart rate at the dosage required for manifestation of the beta-adrenergic blocking activity is considered, the decrease in heart rate in the case of the invention compound A, when administered orally, is low, there being practically no change in heart rate. This decrease was 4 % and 2 %, respectively, in the case of rats and dogs. On the other hand, in the case of the other compounds, this decrease in heart rate ranged from a low of 10 % to as high as 24 %. An especially noteworthy fact is that the invention compound A demonstrates a high decrease in heart rate as in the case with the other compounds when it is administered by means of injection. That is, to say, it is clear that the decrease in heart rate is practically checked only when the invention compound A is administered via the intestinal absorption route as by oral administration.

As indicated hereinabove, the invention compound, when administered via the intestinal route, and particularly orally, demonstrates a higher beta-adrenergic blocking activity than the other beta-adrenergic blocking compounds of similar structure. Further, the side reactions that are evidenced by an analysis of behaviors appear only to an extent comparable to, if not less than, the case of the other compounds. Again, it can be seen that the lethal dose in the case of the invention compound A, when orally administered, is far greater than in the case of the other compounds. When comparisons are made of the degree of safety of the pharmaceutical compounds as indicated by ratio of the dosage at which side reactions appear as shown by the foregoing behavorial analysis to the effective dosage and the ratio of the lethal dosage to the effective dosage, it can be seen that the degree of safety of the invention compounds is about 14 times that of PROPRANOLOL in the case of rats and more than 16 times in the case of dogs. When the degree of safety is compared with the other similar compounds, it ranges from a low of 7 times to as high as 20 times.

The compound B of the formula

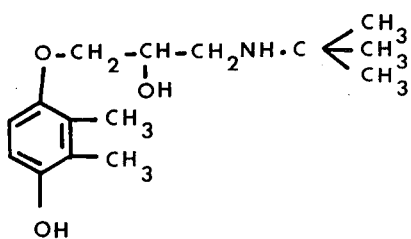

and the compound C of the formula

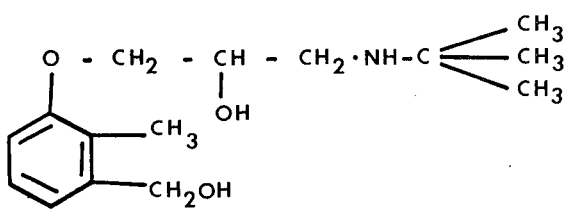

that are main metabolites formed when the invention compound A is administered via the intestinal absorption route also exhibit a higher beta-adrenergic blocking activity than PROPRANOLOL, as indicated in Table 2, below, as well as a lower action of suppressing the heart rate and lesser side reactions.

Table 2

| Compound | Relative beta-adrenergic blocking effectiveness as compared to PROPRANOLOL i.v. | p.o. | $ED_{50}$ in the case of p.o. | Change in heart rate at the dosage required for manifestation of the beta-adrenergic blocking activity No./min. |
|---|---|---|---|---|
| Compound B | 5.5 | 2.5 | 5.5 | +10 (3% increase) |
| do. C | 4.5 | 4.0 | 3.5 | ±0 |

From the results shown in the foregoing table, and especially the fact that the change in heart rate by injection in the case of the compounds B and C is small, the excellent results obtained when the invention compound is administered via the intestinal absorption route as by oral administration, i.e., the high beta-adrenergic blocking activity, the low suppressive action on the heart rate and a minimum of side reactions, as hereinbefore described, are believed to be the result of the synergism of the compound A and its metabolic products, compounds B and C.

In contrast, it is known that when PROPRANOLOL is orally administered 90 % of its is metabolized and the metabolic product thereof has a very weak beta-adrenergic blocking activity (A. Hayes et al. J. Pharmac. Exp. Therap., Vol. 176, page 302 (1971)). Hence, the activity of the invention compound A when administered via the intestinal absorption route as by oral administration is exceedingly unique and astonishing.

Thus, it is apparent from the results of the foregoing experiments that the compound A of the present invention exhibits ideally excellent pharmacological effects when administered via the intestinal absorption route as by oral administration in that despite the fact that it possesses a powerful beta-adrenergic blocking activity it does not demonstrate a heart rate suppressing action as in the case with the other beta-adrenergic blocking chemicals and, in addition, its side reactions are also small.

Recipes for compounding the several forms of the invention pharmaceutical composition to be used for administration via the intestinal absorption route are given below, it being understood, however, that the invention is not to be limited thereby.

Example 1-Recipes for compounding tablets.

| | Milligrams |
|---|---|
| Active compound A | 1.0 |
| Lactose | 88.8 |
| Starch (corn starch) | 10.0 |
| Magnesium stearate | 0.2 |
| Total | 100.0 |

| | |
|---|---|
| Active compound A | 5.0 |
| Lactose | 84.8 |
| Corn starch | 10.0 |
| Talc | 0.2 |
| Total | 100.0 |

Example 2-Recipe for compounding a powder.

| | Milligrams |
|---|---|
| Active compound A | 50 |
| Lactose | 835 |
| Corn starch | 115 |
| Total | 1000 |

Example 3-Recipe for compounding granules

| | Milligrams |
|---|---|
| Active compound A | 5.0 |
| Lactose | 895.0 |
| Corn starch | 1000.0 |

Example 4-Recipe for compounding a syrup.

| | Milligrams |
|---|---|
| Active compound A | 5.0 |
| Sucrose | 600.0 |
| P-oxybenzoic acid | 0.24 |
| P-oxybenzoic acid butyl ester | 0.14 |
| Purified water to make 1 liter | |

Example 5-Recipe for compounding a suppository.

| | Milligrams |
|---|---|
| Active compound A | 5 |
| Cacao butter | 1,995 |
| Total | 2,000 |

When a suppository containing the invention compound A is used, immediate effects can be expected, since intestinal absorption is especially rapid.

While the pharmaceutical composition containing the invention compound A can be used in the range of 0.5 mg to 100 mg per dose, it preferably is administered at a dose of 1 – 5 mg.

EXAMPLE 6 — A CLINICAL TEST USING THE COMPOUND A.

Three angina pectoris patients were administered a daily dose (a 5-mg tablet twice daily in the morning and evening) of the compound A. A test was then conducted on the third day 3 hours after the first administration. Administration of PROPRANOLOL at a daily dosage of 80 mg (40-mg tablet × 2) and also a placebo was carried out with the same schedule. The test was carried out by the double blind method with a cross over test having a rest period of 10 days. The test method consisted of an exercise test utilizing a bicycle ergometer. After measuring the heart rates of the patients before starting the test, the patients were made to pedal the bicycle ergometer until they were seized with an attack of anginal pain, the effectiveness of the chemicals being judged by the time up to the attack and the heart rate at that time. The results are shown in Table 3, below.

Table 3

| | Compound A | | | | PROPRANOLOL | | | | Placebo | | |
|---|---|---|---|---|---|---|---|---|---|---|---|
| Case No. | a) Heart rate before exercise | Exercise time (sec) | b) Heart rate after exercise | Change in heart rate b)−a) | a) Heart rate before exercise | Exercise time (sec) | b) Heart rate after exercise | Change in heart rate b)−a) | a) Heart rate before exercise | Exercise time (sec) | b) Heart rate after exercise | Change in heart rate b)−a) |
| 1 | 81 | 187 | 98 | 17 | 74 | 134 | 109 | 35 | 82 | 117 | 124 | 42 |
| 2 | 76 | 203 | 96 | 20 | 69 | 146 | 96 | 27 | 76 | 110 | 105 | 29 |
| 3 | 84 | 144 | 103 | 19 | 75 | 102 | 102 | 27 | 88 | 96 | 122 | 34 |
| Mean | 80.3 | 178.0 | 99.0 | 18.7 | 72.7 | 127.3 | 102.3 | 29.7 | 82.0 | 107.7 | 117.0 | 55.0 |
| ± S.E. | ± 2.34 | ± 17.62 | ± 2.08 | ± 0.89 | ± 1.86 | ± 13.13 | ± 3.76 | ± 2.67 | ± 3.46 | ± 6.18 | ± 6.03 | ± 3.79 |

As is apparent from the results given in the foregoing table 3, the compound A increases the exercise time up to the time the attack with anginal pains takes place and, in addition, suppresses the increase in the heart rate due to the exercise, as compared with the placebo. The effectiveness of compound A was far greater than that of PROPRANOLOL. A further noteworthy fact was that while the administration of PROPRANOLOL demonstrated a marked suppression of the heart rate, as compared with the placebo, the compound A exhibited practically no suppression of the heart rate.

That is to say, the compound A demonstrated the effects of increasing the exercise time as well as suppression of an increase of the heart rate without suppressing the before-exercise heart rate. Hence, the effects demonstrated by compound A can be said to be ideal.

What is claimed is:

1. A method of treating or preventing coronary disorders in a human by blocking the activity of the beta-adrenergic nerve which comprises administering to a human body in need thereof via the intestinal absorption route in an amount ranging from 0.5 milligrams to 100 milligrams a compound of the formula

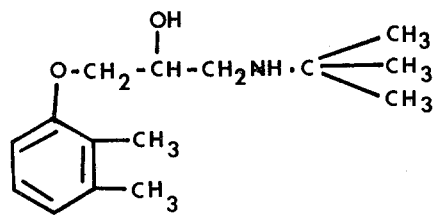

or a pharmaceutically acceptable salt thereof.

2. The method according to claim 1 wherein said compound is administered in the form of a powder composition.

3. The method according to claim 1 wherein said compound is administered in the form of a solution composition.

4. The method according to claim 1 wherein said compound is administered in the form of a suspension composition.

5. The method according to claim 1 wherein said compound is administered in the form of a capsule.

6. The method according to claim 1 wherein said compound is administered in the form of a microcapsule.

7. The method according to claim 1 wherein said compound is administered in the form of granules.

8. The method according to claim 1 wherein said compound is administered in the form of a tablet.

9. The method according to claim 1 wherein the coronary disorder is angina pectoris.

10. The method according to claim 1 wherein said pharmaceutically acceptable salt is an acid addition salt wherein said acid is selected from the group consisting of hydrochloric acid, hydrobromic acid, sulphuric acid, phosphoric acid, methanesulphonic acid, acetic acid, lactic acid, tartaric acid and ascorbic acid.

* * * * *